(12) United States Patent
Araujo Da Silva et al.

(10) Patent No.: US 9,394,380 B2
(45) Date of Patent: *Jul. 19, 2016

(54) GRAFT POLYMER TO WHICH COMBINED NITROGEN MOLECULES ARE GRAFTED

(75) Inventors: José Araujo Da Silva, Clermont-Ferrand (FR); Jean-Michel Favrot, Clermont-Ferrand (FR); Anne Frédérique Salit, Clermont-Ferrand (FR); Nicolas Seeboth, Clermont-Ferrand (FR)

(73) Assignees: COMPAGNIE GENERALE DES ETABLISSEMENTS MICHELIN, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 227 days.

This patent is subject to a terminal disclaimer.

(21) Appl. No.: 13/809,840

(22) PCT Filed: Jul. 12, 2011

(86) PCT No.: PCT/EP2011/061799
§ 371 (c)(1),
(2), (4) Date: Feb. 8, 2013

(87) PCT Pub. No.: WO2012/007441
PCT Pub. Date: Jan. 19, 2012

(65) Prior Publication Data
US 2013/0131279 A1      May 23, 2013

(30) Foreign Application Priority Data

Jul. 13, 2010 (FR) .................... 10 02954

(51) Int. Cl.
| | |
|---|---|
| C08F 8/30 | (2006.01) |
| C08C 19/22 | (2006.01) |
| C08C 19/28 | (2006.01) |
| C07D 233/34 | (2006.01) |
| C07D 233/36 | (2006.01) |
| C08F 36/04 | (2006.01) |

(52) U.S. Cl.
CPC .............. *C08C 19/22* (2013.01); *C07D 233/34* (2013.01); *C07D 233/36* (2013.01); *C08C 19/28* (2013.01); *C08F 36/04* (2013.01); *C08F 8/30* (2013.01)

(58) Field of Classification Search
CPC ........... C08C 19/22; C08C 19/28; C08F 8/30; C08F 8/32; C08F 8/48; C08K 5/21; C08K 5/3472; C08K 5/3475; C08K 5/315; C08K 5/29; C08K 5/32
USPC ............. 525/331.9, 332.1, 333.1, 333.2, 374, 525/375, 376, 377
See application file for complete search history.

(56) References Cited

U.S. PATENT DOCUMENTS

| | | | |
|---|---|---|---|
| 5,128,416 A | 7/1992 | Imai et al. | |
| 5,329,005 A | 7/1994 | Lawson et al. | |
| 5,393,721 A | 2/1995 | Kitamura et al. | |
| 7,186,845 B2 | 3/2007 | Fukushima et al. | |
| 2004/0106744 A1 | 6/2004 | Chino et al. | |
| 2005/0239639 A1 | 10/2005 | Monteil et al. | |
| 2006/0084730 A1* | 4/2006 | Fukushima et al. | 524/90 |
| 2006/0199917 A1 | 9/2006 | Chino | |
| 2011/0183098 A1* | 7/2011 | Hidalgo et al. | 428/36.9 |

FOREIGN PATENT DOCUMENTS

| | | |
|---|---|---|
| EP | 0 341 496 A | 11/1989 |
| EP | 0 590 491 A | 4/1994 |
| EP | 0 593 049 A | 4/1994 |
| JP | 2008-208163 A | 9/2008 |
| WO | WO 2004/035639 A1 | 4/2004 |
| WO | WO-2010/031956 A1 * | 3/2010 |
| WO | WO 2010/031956 A1 | 3/2010 |

OTHER PUBLICATIONS

International Search Report (PCT/ISA/210) issued on Oct. 5, 2011, by the European Patent Office as the International Searching Authority for International Application No. PCT/EP2011/061799.
M. Galimberti et al., "Elastomeric Compounds with Silica. Lower Hysteresis in the Presence of Functionalised Isoprene Oligomers", Macromolecular Symposia, Mar. 13, 2006, vol. 234 (abstract only).

* cited by examiner

*Primary Examiner* — Roberto Rabago
(74) *Attorney, Agent, or Firm* — Dickinson Wright PLLC

(57) ABSTRACT

The present invention relates to a modified polymer obtained by grafting of a compound comprising at least one group Q and at least one group A, bonded together by at least, and preferably, one "spacer" group Sp in which:
Q comprises a dipole containing at least, and preferably, one nitrogen atom, capable of being grafted onto the polymer chain by [1,3]-dipolar cycloaddition,
A comprises an associative group comprising at least one nitrogen atom,
Sp is an atom or a group of atoms forming a bond between Q and A.

17 Claims, No Drawings

GRAFT POLYMER TO WHICH COMBINED NITROGEN MOLECULES ARE GRAFTED

The present invention relates to a polymer modified by grafting of nitrogen-containing associative molecules comprising at least one unit making them capable of combining with each other or with a filler via non-covalent bonds.

Since fuel savings and the need to protect the environment have become a priority, it is desirable to produce mixtures having good mechanical properties and a hysteresis which is as low as possible in order to be able to use them in the form of rubber compositions which can be used for the manufacture of various semi-finished products entering into the composition of tyre casings, such as for example underlayers, sidewalls, treads, and to obtain tyres having reduced rolling resistance.

The reduction of the hysteresis of the mixtures is a permanent objective which should however be achieved while preserving the capacity of the mixtures to be used.

To achieve the objective of reducing hysteresis, many solutions have been tested. In particular, mention may be made of the modification of the structure of diene polymers and copolymers after polymerization by means of functionalizing, coupling or starring agents or post-polymerization with the aim of obtaining good interaction between the polymer thus modified and the filler, whether this is carbon black or a reinforcing inorganic filler.

For example, patent applications EP-A-0 590 491 and EP-A-0 593 049 describe polymers bearing amine functional groups which allow better interaction between the polymer and carbon black.

Mention may also be made of U.S. Pat. No. 5,015,692 or of patent EP 0 341 496 which provide a process for functionalizing elastomers with compounds such as phosphorus compounds, nitro compounds, aminosilanes, acrylamides, aminovinylsilanes, where appropriate combined with coupling or starring with a compound based on silicon or tin, in order to improve the impact elasticity of rubber compositions containing them. These patents describe in particular rubber compositions reinforced with carbon black containing a polybutadiene functionalized at the chain end with an alkoxysilane bearing an amine group.

In the context of post-polymerization functionalization, documents U.S. Pat. No. 7,186,845 B2 and JP2008208163 also describe the modification of polymers comprising diene units with nitrogen-containing dipolar compounds additionally comprising a heterocycle, the said heterocycle itself comprising a nitrogen atom, and an oxygen and/or sulphur atom. More particularly, the compounds described are nitrones bearing oxazoline, thiazoline functional groups, such as for example ((2-oxazolyl)-phenyl-N-methylnitrone)

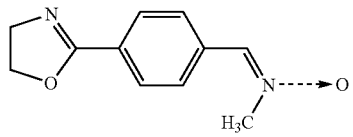

When diene polymers are made to react with such compounds, the resultant polymers will bear oxazoline or thiazoline rings.

These rings, which are present on the polymer, are capable of reacting, in turn, with surface functional groups of the fillers (such as carbon black or silica) with which the polymers are mixed. This reaction leads to the establishment of covalent bonds between the polymer modified with the coupling agent and the filler because of the opening of the oxazoline or thiazoline ring. Indeed, as is described in the document U.S. Pat. No. 7,186,845B2, the oxazoline and/or thioazoline rings are capable of opening in the presence of a nucleophile which may for example be present at the surface of the filler.

These polymers confer in particular a reduced hysteresis on the rubber compositions containing them.

Moreover, the document published under the number WO2010/031956 describes elastomers functionalized with nitrogen-containing heterocycles. The production of such modified polymers is realized by virtue of the addition of modifying agents having a reactive group, on the one hand, and a nitrogen-containing heterocycle, on the other. The grafting of the reactive group of the modifying agent is carried out on functional groups already present on the polymer, such as epoxys, acids, anhydrides and the like. The production of elastomers having nitrogen-containing heterocycles therefore requires the use of prefunctionalized elastomers.

Among the associative groups envisaged in this document, mention may be made of the imidazolidinyl, triazolyl, triazinyl, bis-ureyl and ureido-pyrimidyl groups.

Unexpectedly, the applicant has found that the modification of a polymer with groups, other than the thiazolines and oxazolines mentioned in the above patents, which are hardly sensitive to nucleophilic attacks, makes it possible to obtain a reduction in hysteresis compared with an unmodified polymer.

The subject of the invention is a polymer modified by grafting of a compound comprising at least one group Q and at least one group A, bonded together by at least, and preferably, one "spacer" group Sp in which:
  Q comprises a dipole containing at least, and preferably, one nitrogen atom,
  A comprises an associative group comprising at least one nitrogen atom,
  Sp is an atom or a group of atoms forming a bond between Q and A.

A polymer modified by grafting of a compound as defined above, mixed with fillers, makes it possible to ensure a good polymer-filler interaction which is beneficial for the final properties of the polymer.

The subject of the invention is also a process which makes it possible to prepare the modified polymer defined above by grafting compounds comprising nitrogen-containing associative groups with a good grafting yield.

Accordingly, the subject of the invention is a polymer modified by grafting a compound comprising at least one group Q and at least one group A, bonded together by at least, and preferably, a "spacer" group Sp as described above.

The expression "polymer" is understood to mean according to the invention any polymer containing at least one unsaturation or double bond capable of reacting with the compound described above.

Preferably, the polymers of the present invention are diene elastomers.

These diene elastomers may be classified in a known manner into two categories, those that are said to be essentially unsaturated and those that are said to be essentially saturated. These two categories of diene elastomers may be envisaged in the context of the invention.

An essentially saturated diene elastomer has a low or very low amount of motifs or units of diene origin (conjugated dienes) which is always less than 15% (mol %). Accordingly, for example, butyl rubbers or EPDM type copolymers of dienes and alpha-olefins enter into the definition of essentially saturated diene elastomers.

By contrast, the expression "essentially unsaturated diene elastomer" is understood to mean a diene elastomer that is at least partially derived from conjugated diene monomers, having an amount of motifs or units of diene origin (conjugated dienes) which is greater than 15% (15 mol %). In the category of "essentially unsaturated" diene elastomers, the expression "highly unsaturated" diene elastomer is understood to mean in particular a diene elastomer having an amount of units of diene origin (conjugated dienes) which is greater than 50%.

The expression "diene elastomer capable of being used in the invention" is understood to mean more particularly:
(a)—any homopolymer obtained by polymerization of a conjugated diene monomer having from 4 to 12 carbon atoms;
(b)—any copolymer obtained by copolymerization of one or more dienes conjugated with each other or with one or more aromatic vinyl compounds having from 8 to 20 carbon atoms;
(c)—a ternary copolymer obtained by copolymerization of ethylene, of an α-olefin having 3 to 6 carbon atoms with an unconjugated diene monomer having from 6 to 12 carbon atoms, such as for example the elastomers obtained from ethylene, propylene with an unconjugated diene monomer of the abovementioned type such as in particular hexadiene-1,4, ethylidenenorbornene, dicyclopentadiene; such polymers are described in particular in the documents WO 2004/035639A1 and US 2005/0239639A1;
(d)—an isobutene and isoprene copolymer (butyl rubber), as well as the halogenated, in particular chlorinated or brominated, versions of this type of copolymer.

Although it applies to any type of diene elastomer, the use of at least one diene elastomer of the highly unsaturated type, in particular of the (a) or (b) type above, is preferred.

As conjugated dienes butadiene-1,3, 2-methyl-1,3-butadiene, 2,3-di(C1-C5 alkyl)-1,3-butadienes such as for example 2,3-dimethyl-1,3-butadiene, 2,3-diethyl-1,3-butadiene, 2-methyl-3-ethyl-1,3-butadiene, 2-methyl-3-isopropyl-1,3-butadiene, an aryl-1,3-butadiene, 1,3-pentadiene, 2,4-hexadiene are in particular suitable. As vinylaromatic compounds, styrene, ortho-, meta-, para-methylstyrene, the "vinyl-toluene" commercial mixture, para-tert-butylstyrene, methoxystyrenes, chlorostyrenes, vinylmesitylene, divinylbenzene, vinylnaphthalene, are for example suitable.

The copolymers may contain between 99% and 20% by weight of diene units and between 1% and 80% by weight of vinylaromatic units. The elastomers may have any microstructure which depends on the polymerization conditions used, in particular on the presence or absence of a modifying and/or randomizing agent and on the quantities of modifying randomizing agent used. The elastomers may be for example block, random, sequenced or microsequenced elastomers, and may be prepared as a dispersion, an emulsion or a solution; they may be coupled and/or starred or functionalized with a coupling and/or starring or functionalizing agent.

The diene elastomers selected from the group consisting of polybutadienes (BR), synthetic polyisoprenes (IR), natural rubber (NR), butadiene copolymers, isoprene copolymers and mixtures of these elastomers are in particular suitable. Such copolymers are more preferably selected from the group consisting of butadiene-styrene (SBR) copolymers, isoprene-butadiene (BIR) copolymers, isoprene-styrene (SIR) copolymers, isoprene-butadiene-styrene (SBIR) copolymers and mixtures of such copolymers.

According to the invention, the polymer having at least one unsaturation or double bond is modified by grafting of a compound, also called modifying agent, comprising at least one group Q and at least one group A, bonded together by at least, and preferably, one "spacer" group in which:
Q comprises a dipole containing at least, and preferably, one nitrogen atom,
A comprises an associative group comprising at least one nitrogen atom,
Sp is an atom or a group of atoms forming a bond between Q and A.

The expression "dipole" is understood to mean a functional group capable of forming a 1,3-dipole addition onto an unsaturated carbon-carbon bond.

The expression "associative group" is understood to mean groups capable of combining with each other via hydrogen, ionic and/or hydrophobic bonds. According to a preferred embodiment of the invention, they are groups capable of combining via hydrogen bonds.

When the associative groups are capable of combining via hydrogen bonds, each associative group comprises at least one donor "site" and one acceptor site in relation to the hydrogen bond such that two identical associative groups are self-complementary and may combine with each other, forming at least two hydrogen bonds.

The associative groups according to the invention are also capable of combining via hydrogen, ionic and/or hydrophobic bonds with functional groups present on fillers.

The compounds according to the invention comprising a group Q and a "spacer" group and an associative group may for example be represented by the following formula (Ia):

A-Sp-Q (Ia).

The compounds according to the invention comprising a group Q, a "spacer" group and two associative groups may for example be represented by the following formula (Ib):

Likewise, the compounds according to the invention comprising two groups Q, a "spacer" group and an associative group may for example be represented by the following formula (Ic):

According to the same principle, the compounds according to the invention comprising two groups Q, a "spacer" group and two associative groups may for example be represented by the following formula (Id):

Preferably, the associative group is chosen from an imidazolidinyl, ureyl, bis-ureyl, ureido-pyrimidyl, triazolyl group.

Preferably, the group A corresponds to one of the following formulae (II) to (VI):

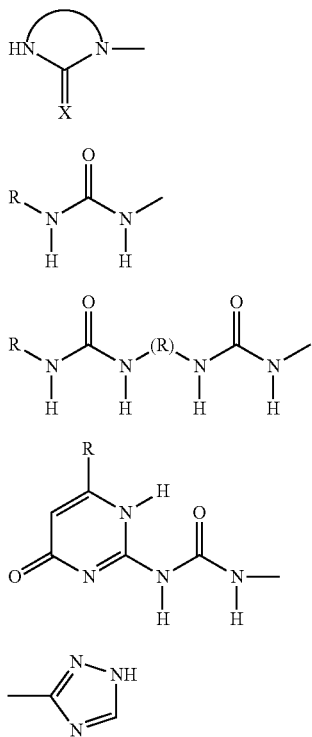

where:
R denotes a hydrocarbon group which may optionally contain heteroatoms,
X denotes an oxygen or sulphur atom or a group —NH, preferably an oxygen atom.

Preferably, the group A comprises a 5- or 6-membered, di- or trinitrogen-containing, preferably dinitrogen-containing, heterocycle comprising at least one carbonyl functional group.

Likewise, preferably still, the group A comprises an imidazolidinyl group of formula (II).

The group Q is capable of bonding to a polymer chain comprising at least one unsaturation or double bond by a covalent bond (grafting). Preferably, the group Q comprises a nitryl oxide, nitrone or nitrile imine functional group which can bond to a polymer bearing at least one unsaturation, by a [3+2] type cycloaddition.

Preferably, the group Q is a group of the following formula (VII), (VIII) or (IX)

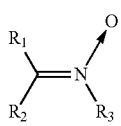

(VII)

$R_4$—C≡N→O (VIII)

$R_5$—C≡N→N—$R_6$ (IX)

in which R1 to R6 are independently selected from a spacer group Sp, a hydrogen atom, a linear or branched C1-C20 alkyl group, a linear or branched C3-C20 cycloalkyl group, a linear or branched C6-C20 aryl group and a group of formula (X)

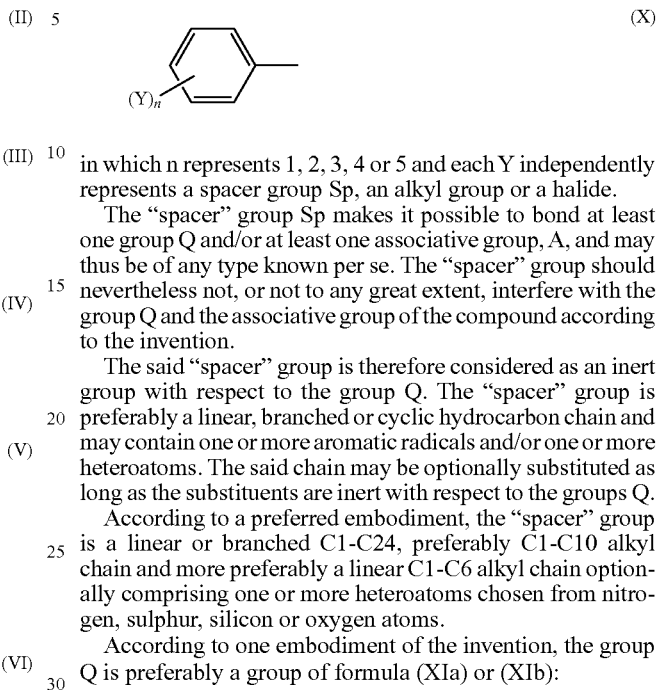

(X)

in which n represents 1, 2, 3, 4 or 5 and each Y independently represents a spacer group Sp, an alkyl group or a halide.

The "spacer" group Sp makes it possible to bond at least one group Q and/or at least one associative group, A, and may thus be of any type known per se. The "spacer" group should nevertheless not, or not to any great extent, interfere with the group Q and the associative group of the compound according to the invention.

The said "spacer" group is therefore considered as an inert group with respect to the group Q. The "spacer" group is preferably a linear, branched or cyclic hydrocarbon chain and may contain one or more aromatic radicals and/or one or more heteroatoms. The said chain may be optionally substituted as long as the substituents are inert with respect to the groups Q.

According to a preferred embodiment, the "spacer" group is a linear or branched C1-C24, preferably C1-C10 alkyl chain and more preferably a linear C1-C6 alkyl chain optionally comprising one or more heteroatoms chosen from nitrogen, sulphur, silicon or oxygen atoms.

According to one embodiment of the invention, the group Q is preferably a group of formula (XIa) or (XIb):

(XIa)

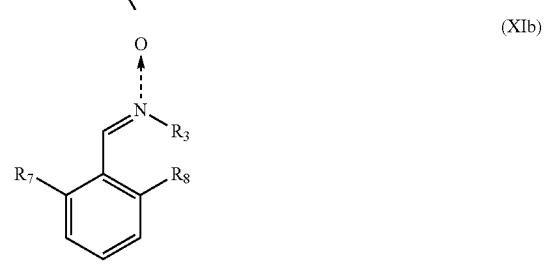

(XIb)

in which R7 and R8 independently represent a hydrogen or a C1-C5 alkyl group, an alkoxyl or a halide and preferably R7 and R8 independently represent an alkyl group or a halide, and more preferably R7 and R8 independently represent a methyl group or a chlorine atom, R3 is as defined above and the group A is a group of formula (XII):

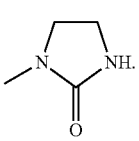

(XII)

Preferably, the compound intended for grafting the polymer in accordance with the invention is then selected from the compounds of the following formulae (XIII) to (XXI):

(XIII) (XIV) (XV) (XVI) (XVII)
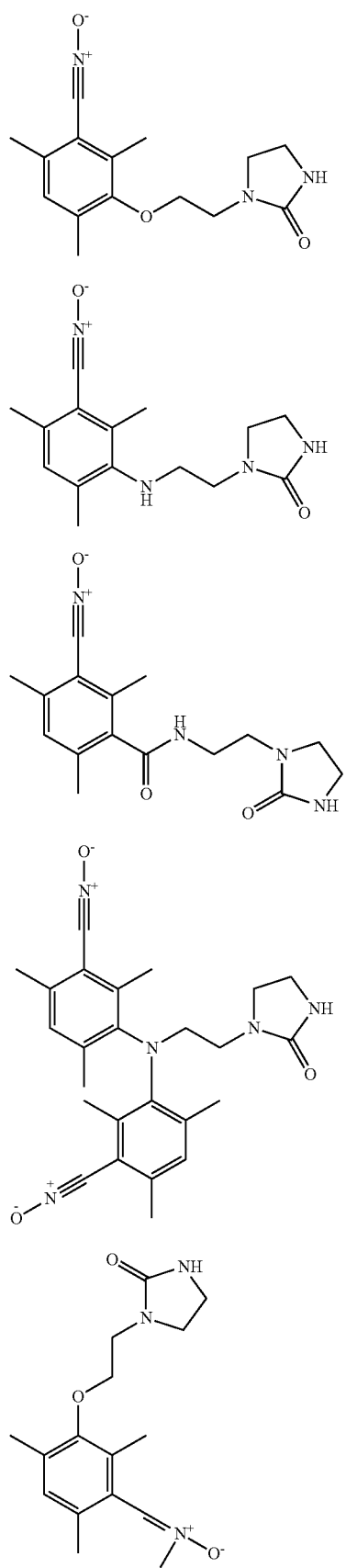
(XVIII)
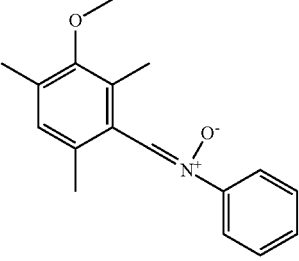
(XIX)
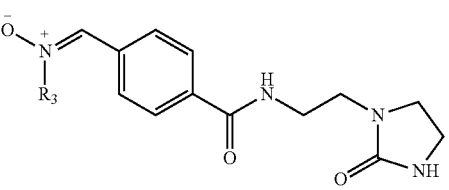
R3 is as defined above
(XX)
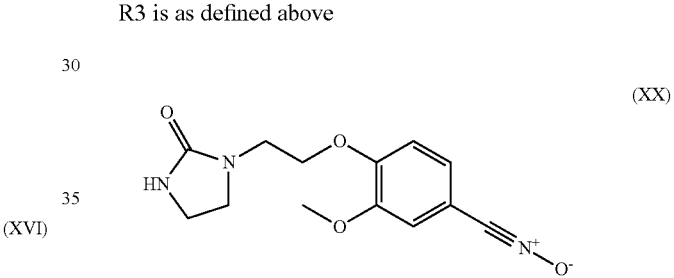
(XXI)
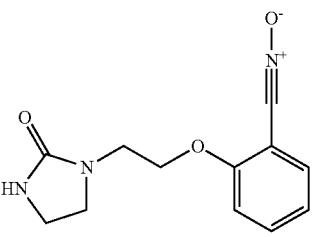
According to another embodiment of the invention, the compound intended for grafting the polymer in accordance with the invention is selected from the compound of the following formulae (XXII) to (XXIII):
(XXII)
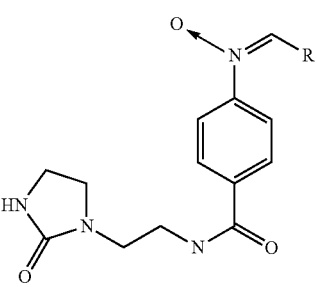

-continued

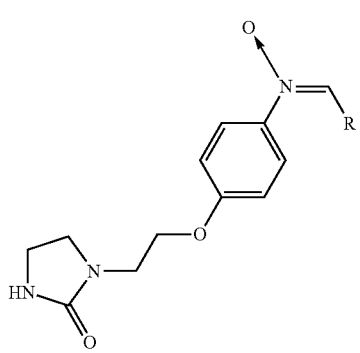
(XXIII)

in which

R is chosen from a spacer group Sp, a hydrogen atom, a linear or branched C1-C20 alkyl group, a linear or branched C3-C20 cycloalkyl group, a linear or branched C6-C20 aryl group, and a group of formula (X)

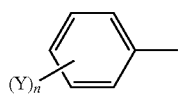
(X)

in which n represents 1, 2, 3, 4 or 5 and each Y independently represents a spacer group Sp, an alkyl group or a halide.

According to a preferred embodiment, the amount of modifying agent varies from 0.01 to 50 mol %, preferably from 0.01 to 5 mol %.

The subject of the invention is also the process for the preparation of the graft elastomer described above.

The grafting of the polymer is carried out by reacting the said polymer with the reactive group(s) carried by the modifying agent. During this reaction, this or these reactive group(s) form(s) covalent bonds with the polymer chain. The grafting yield is particularly high, preferably greater than 60%, and more preferably still greater than 80%.

The grafting of the modifying agent is carried out by [3+2] cycloaddition of the reactive group(s) of the modifying agent and one or more double bonds of the polymer chain. The mechanism of the cycloaddition may be illustrated by the following equations:

cycloaddition of a nitrile oxide onto an unsaturation or a double bond of the polymer (here polyisoprene)

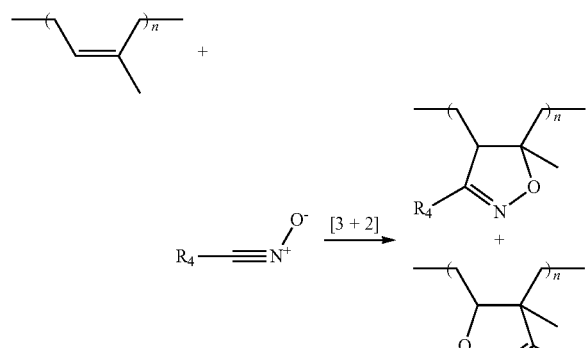

cycloaddition of a nitrone onto an unsaturation or a double bond of the polymer (here polyisoprene)

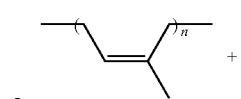

cycloaddition of a nitrile imine onto an unsaturation or a double bond of the polymer (here polyisoprene)

The substituents R are as described above.

The grafting of the modifying agent may be carried out in the mass, for example in an internal mill or an external mill such as an open mill, or in solution. The grafting process may be carried out in solution continuously or batchwise. The polymer thus modified may be separated from its solution by any means known to a person skilled in the art and in particular by a steam stripping operation.

The invention and its advantages will be easily understood in the light of the examples of implementation which follow.

EXAMPLES OF IMPLEMENTATION

The structural analysis and the determination of the molar purities of the synthesis molecules are carried out by NMR analysis. The spectra are acquired on a Bruker Avance 500 MHz spectrometer equipped with a "broad band" probe BBIz-grad 5 mm. The quantitative 1H NMR experiment uses a 30° single pulse sequence and a repeat delay of 3 seconds between each of the 64 acquisitions. The samples are solubilized in deuterated dimethylsulphoxide (DMSO). This solvent is also used for the lock signal. The calibration is performed on the signal of the protons of the deuterated DMSO at 2.44 ppm relative to a TMS reference at 0 ppm. The $^1$H NMR spectrum coupled with 2D 1H/13C HSQC and 1H/13C HMBC experiments allow the structural determination of the molecules (cf. attribution tables). The molar quantifications are carried out starting with the quantitative 1D 1H NMR spectrum.

Infrared measurement makes it possible to validate the presence of the nitrile oxide group carried by an aromatic. The spectra are acquired on a Fourier transform spectrometer VERTEX 70 equipped with a DTGS detector. The spectra are acquired in 32 scans between 4000 cm-1 and 400 cm-1 with a resolution of 2 cm-1. The samples are prepared in the form of KBr pellets. The nitrile oxide functional group carried by the aromatic is characterized by a band at 2295 cm-1.

Analysis by mass spectrometry is performed with direct injection by an electrospray ionization mode (DI/ESI). The analyses were performed on a Bruker HCT spectrometer (flow rate 600 µL/min, nebulizer gas pressure 10 psi, flow rate of the nebulizer gas 4 L/min).

The determination of the molar amount of grafted nitrile oxide compound is performed by NMR analysis. The spectra are acquired on a BRUKER 500 MHz spectrometer equipped with a "broad band" probe BBIz-grad 5 mm. The quantiative $^1H$ NMR experiment uses a 30° single pulse sequence and a repeat delay of 3 seconds between each acquisition. The samples are solubilized in carbon sulphide ($CS_2$). 100 µL of deuterated cyclohexane ($C_6D_{12}$) are added for the lock signal.

The $^1H$ NMR spectrum makes it possible to quantify the grafted nitrile oxide units by integration of the signals characteristic of the $CH_2N$ and $CH_2O$ protons which appear at a chemical shift of between δ=3.1-3.8 ppm.

The 2D $^1H$-$^{13}C$ HSQC NMR spectrum makes it possible to verify the nature of the grafted unit by means of the chemical shifts of the carbon and proton atoms.

Example 1

Modification of an SBR by Grafting of 2,4,6-trimethyl-3-(2-(2-oxoimidazolidin-1-yl)ethoxy)nitrile oxide 1.1—Preparation of the Modifying Agent a) Preparation of 1-(2-(3'-nitrileoxymesityl-1'-oxy)ethyl)imidazolidin-2-one

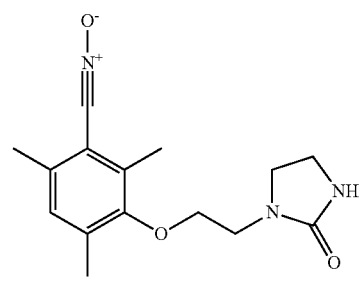 [SMILES: Cc1cc(C)c(OCCN2CCNC2=O)c(C)c1C#[N+][O-]]

This compound may be prepared from hydroxyethylimidazolidone mesitol according to the following synthesis scheme.

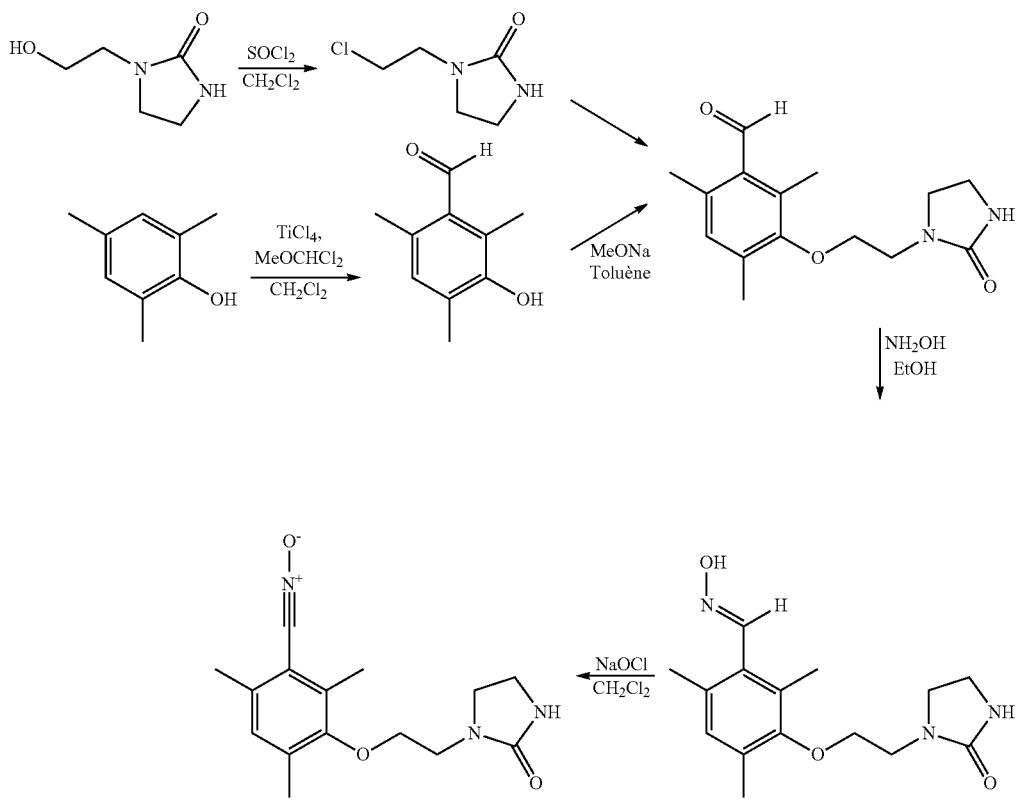

b) Preparation of 3-hydroxy-2,4,6-trimethylbenzaldehyde

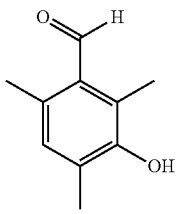

This compound may be obtained according to a procedure described in the following article: Yakubov, A. P.; Tsyganov, D. V.; Belen'kii, L. I.; Krayushkin, M. M.; *Bulletin of the Academy of Sciences of the USSR, Division of Chemical Science* (English Translation); vol. 40; nb. 7.2; (1991); p. 1427-1432; Izvestiya Akademii Nauk SSSR, Seriya Khimicheskaya; nb. 7; (1991); p. 1609-1615.

c) Preparation of 1-(2-chloroethyl)imidazolidin-2-one

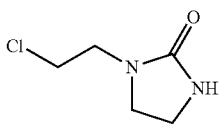

This product is described in the article Nagarajan K, Arya V. P., Shah R. K.; *Indian Journal of Chemistry, Section B: Organic Chemistry Including Medicinal Chemistry*; 21; 10; 1982; 928-940.

To a solution of 1-(2-hydroxyethyl)imidazolidin-2-one (50.0 g, 0.39 mol) in dichloromethane (250 mL) is added dropwise, at room temperature, thionyl chloride (34 mL, 0.47 mol) over 35 minutes. At the end of the addition, the temperature of the reaction medium is 35° C. The reaction medium is kept at a temperature of 35-40° C. for 2.5 hours. After evaporation under reduced pressure ($T_{bath}$ 35° C., 15-17 mbar), the crude product is obtained (67 g). This crude product is crystallized from a mixture of acetone and petroleum ether (35 g per 950 mL of acetone and 820 mL of petroleum ether at −24° C. for 10 to 15 hours). The crystals are filtered, washed with petroleum ether (twice 40 mL) and then dried for 10 to 15 hours under atmospheric pressure at room temperature.

A white solid (33.3 g, yield 66%) having a melting point of 93° C. is obtained. The molar purity is greater than 97% ($^1$H NMR).

A $^1$H and $^{13}$C NMR characterization is presented in the following table 1.

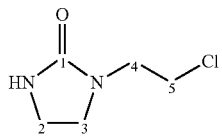

TABLE 1

| Atom | δ $^1$H (ppm) + mult. | δ $^{13}$C (ppm) |
|---|---|---|
| 1 | — | 162.1 |
| 2 | 3.17 (t) | 37.5 |
| 3 | 3.33 (t) | 44.7 |
| 4 | 3.29 (t) | 45.0 |
| 5 | 3.62 (t) | 42.4 |

Solvent used: DMSO - Calibration on the DMSO signal at 2.44 ppm for $^1$H, 39.5 ppm for $^{13}$C.

d) Preparation of 2,4,6-trimethyl-3-(2-(2-oxoimidazolidin-1-yl)ethoxy)benzaldehyde

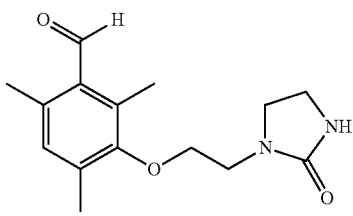 [SMILES: Cc1cc(C)c(OCCN2CCNC2=O)c(C)c1C=O]

To a solution of sodium (1.63 g, 0.071 mol) in methanol (60 mL) is added dropwise 3-hydroxy-2,4,6-trimethylbenzaldehyde (11.90 g, 0.073 mol) in anhydrous toluene (300 mL). The mixture is heated under reflux and then the methanol is distilled off (volume of azeotropic mixture collected 80-90 mL). After returning to 80-90° C., (2-chloroethyl)imidazolidin-2-one (10.45 g, 0.070 mol) is added all at once to the reaction medium. After heating for 7 hours under reflux, the solvents are evaporated under reduced pressure ($T_{bath}$ 50° C., 25 mbar). Dichloromethane (150 mL) and water (30 mL) are added to the mixture obtained. The organic phase is then washed twice with water (20 mL). After drying over $Na_2SO_4$, the dichloromethane is evaporated under reduced pressure ($T_{bath}$ 35° C., 33 mbar). Petroleum ether (3 times 50 mL) and water (50 mL) are added to the mixture obtained (24 g) and the precipitate obtained is filtered and washed on the filter with water (15 mL) and petroleum ether (twice 15 mL).

The product obtained is repurified by washing the product in solution in dichloromethane (80 mL) with a 4% NaOH solution in water (3 times 60 mL). After evaporation of the solvents under reduced pressure, the product is precipitated from petroleum ether. The precipitate is filtered and dried for 15 to 20 hours under atmospheric pressure at room temperature.

A white solid (8.55 g, yield 44%) having a melting point of 139° C. is obtained. The molar purity is greater than 94% (1H HMR).

A $^1$H and $^{13}$C NMR characterization is presented in the following table 2.

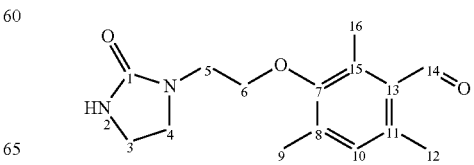

TABLE 2

| Atom | δ $^1$H (ppm) + mult. | δ $^{13}$C (ppm) |
|---|---|---|
| 1 | — | 163.1 |
| 2 | ~4.74 (s) | — |
| 3 | 3.40 (t) | 38.1 |
| 4 | 3.65 (t) | 46.8 |
| 5 | 3.52 (t) | 43.9 |
| 6 | 3.79 (t) | 71.3 |
| 7 | — | 153.9 |
| 8 | — | * |
| 9 | 2.23/2.46 (s) | 16.5/19.8 |
| 10 | 6.84 | 131.7 |
| 11 | — | * |
| 12 | 2.23/2.46 (s) | 16.5/19.8 |
| 13 | — | * |
| 14 | ~10.46 (s) | 193.0 |
| 15 | — | * |
| 16 | 2.46 (s) | 12.1 |

*131.4/133.5/136.6/136.7 ppm: The chemical shifts for the $^{13}$C of the aromatic ring are not attributed.
Solvent used: CDCl$_3$ - Calibration on the chloroform signal at 7.2 ppm for $^1$H, 77 ppm for $^{13}$C.

e) Preparation of 2,4,6-trimethyl-3-(2-(2-oxoimidazolidin-1-yl)ethoxy)benzaldehyde oxime

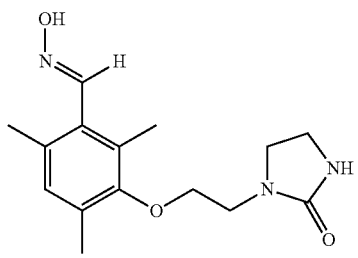 [SMILES: Cc1cc(C)c(OCCN2CCNC2=O)c(C)c1/C=N/O]

To a solution of 2,4,6-trimethyl-3-(2-(2-oxoimidazolidin-1-yl)ethoxy)benzaldehyde (7.90 g, 0.029 mol) in ethanol (70 mL) kept at a temperature of 45° C. is added an aqueous hydroxylamine solution (2.83 g, 0.043 mol, 50% in water) in ethanol (10 mL). The reaction medium is then stirred for 2.5 hours at a temperature between 50 and 55° C. The solvent is evaporated under reduced pressure (T$_{bath}$ 37° C., 35 mbar). Petroleum ether (80 mL) is added to a crude product obtained. The precipitate obtained is filtered, washed with petroleum ether (twice 20 mL) and dried for 15 to 20 hours under atmospheric pressure at room temperature.

A white solid (7.82 g, yield 94%) having a melting point of 165° C. is obtained. The molar purity is greater than 84% (the remaining 16% comprise in particular 7 mol % EtOH) based on $^1$H NMR.

A $^1$H and $^{13}$C NMR characterization is presented in the following table 3.

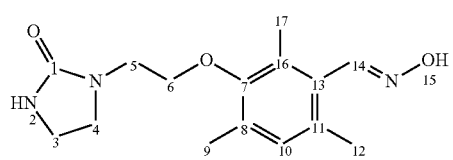

TABLE 3

| Atom | δ $^1$H (ppm) + mult. | δ $^{13}$C (ppm) |
|---|---|---|
| 1 | — | 162.0 |
| 2 | ~6.30 (s) | — |
| 3 | 3.19 (t) | 37.1 |
| 4 | 3.44 (t) | 45.5 |
| 5 | 3.34 (t) | 43.2 |
| 6 | 3.69 (t) | 70.3 |
| 7 | — | 153.5 |
| 8 | — | * |
| 9 | 2.14 (s) | 15.4 |
| 10 | — | 130.5 |
| 11 | — | * |
| 12 | 2.18 (s) | 19.9 |
| 13 | — | * |
| 14 | ~8.20 (s) | 147.4 |
| 15 | ~11.10 (s) | — |
| 16 | — | * |
| 17 | 2.17 (s) | 12.9 |

*129.3/129.5/131.9 ppm: The chemical shifts of the $^{13}$C of the aromatic ring are not attributed, three signals are detected (probably two carbons under one and the same signal).
Solvent used: DMSO - Calibration on the DMSO signal at 2.44 ppm for $^1$H, 39.5 ppm for $^{13}$C.

f) Preparation of 2,4,6-trimethyl-3-(2-(2-oxoimidazolidin-1-yl)ethoxy)nitrile oxide, Compound According to the Invention

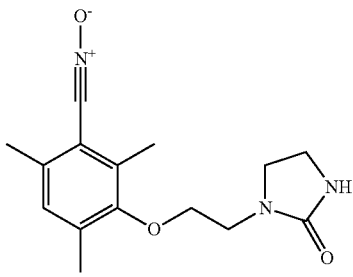 [SMILES: Cc1cc(C)c(OCCN2CCNC2=O)c(C)c1C#[N+][O-]]

To an oxime solution previously prepared (6.00 g, 0.021 mol) in dichloromethane (250 mL), at the temperature of 2° C., is added dropwise an aqueous NaOCl solution (4% of active chlorine, 52 mL) over 5-7 minutes. The temperature of the reaction medium is kept between 0 and −4° C. The reaction medium is then stirred for 3 hours at a temperature between 0 and 5° C. The organic phase is then separated. The aqueous phase is extracted with dichloromethane (twice 15 mL). The organic phases are combined and then washed with water (twice 20 mL), dried with Na$_2$SO$_4$. The volume of solvent is reduced by evaporation under reduced pressure (T$_{bath}$ 22° C., 220 mbar) to 50-60 mL. Petroleum ether (75 mL) is then added and the solution is placed at −18° C. for 10-15 hours. The precipitate obtained is filtered and washed with an ethyl acetate/petroleum ether mixture (½) (10 mL) and finally dried for 10-15 hours under atmospheric pressure at room temperature.

A white solid (4.70 g, yield 79%) having a melting point of 156° C. is obtained.

The molar purity is greater than 85% ($^1$H NMR).

A $^1$H and $^{13}$C NMR characterization is presented in the following table 4.

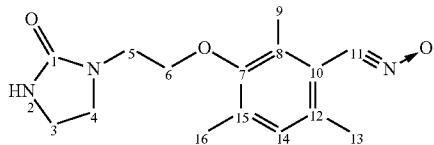

TABLE 4

| Atom | δ $^1$H (ppm) + mult. | δ $^{13}$C (ppm) |
|---|---|---|
| 1 | — | Not detected, not attributed |
| 2 | ~4.59 (s) | — |
| 3 | 3.41 (t) | 38.3 |
| 4 | 3.64 (t) | 47.0 |
| 5 | 3.51 (t) | 44.1 |
| 6 | 3.79 (t) | 71.5 |
| 7 | — | 153.6 |
| 8 | — | 134.4/137.3* |
| 9 | 2.32 (s) | 14.8 |
| 10 | — | 112.8 |
| 11 | — | Not detected, not attributed |
| 12 | — | 134.4/137.3* |
| 13 | 2.31 (s) | 20.2 |
| 14 | 6.85 (s) | 130.3 |
| 15 | — | 134.4/137.3* |
| 16 | 2.20 (s) | 16.4 |

*The aromatic carbons 8, 12 and 15 are not attributed. Two signals are observed by $^{13}$C NMR, there are probably two carbons which come out under the same signal.
The functional group - C≡N→O exhibits a characteristic IR band at 2295 cm$^{-1}$.
Solvent used: CDCl$_3$ - Calibration on the chloroform signal at 7.2 ppm for $^1$H, 77 ppm for $^{13}$C.

1.2—Grafting of the Modifying Agent onto SBR in the Mass

The modifying agent previously obtained is used.
2,4,6-Trimethyl-3-(2-(2-oxoimidazolidin-1-yl)ethoxy)nitroxide (2.72 g, 9.4 mmol), having an NMR purity of 86 mol %, is incorporated into 30 g of SBR (containing 26% by weight of styrene and 24% by weight of butadiene-1,2 unit and having an Mn=162 900 g/mol and a V$_p$=1.15) on a cylinder tool (external mill at 30° C.). The mixture is homogenized in 15 passes.

This mixing phase is followed by a heat treatment in a press at a pressure of 10 bar. The durations and the temperatures of this second stage were modulated.

$^1$H NMR analysis made it possible to determine the molar amount of grafting and the molar yield of grafting which are reported in the following table:

TABLE 5

| time | T° | NMR level (mol %) | yield |
|---|---|---|---|
| 5 min | 110 | 1.55 | 90% |
| 10 min | 110 | 1.55 | 90% |
| 5 min | 150° C. | 1.55 | 90% |
| 10 min | 150° C. | 1.54 | 90% |

1.3—Grafting of the Modifying Agent onto SBR in Solution 2 g of SBR (containing 26% by weight of styrene and 24% by weight of butadiene-1,2 unit and having an Mn=162 900 g/mol and a Vp=1.15) are dissolved in solution in 50 mL of dichloromethane. A solution of 60 mg (0.2 mmol) of 2,4,6-trimethyl-3-(2-(2-oxoimidazolidin-1-yl)ethoxy)nitrile oxide in 5 mL of dichloromethane is added to the polymer solution and the reaction medium is stirred for 24 h at the reflux temperature of the dichloromethane.

The polymer is then coagulated in an acetone/methanol mixture. The polymer is dissolved in toluene and then subjected to an antioxidant treatment by addition of 0.2 phr of 4,4'-methylene-bis-2,6-tert-butylphenol and 0.2 phr of N-(1,3-dimethylbutyl)-N'-phenyl-p-phenylenediamine. The polymer is dried under vacuum for 48 h at 60° C.

$^1$H NMR analysis shows that the polymer was modified in an amount of 1 mol %, which is still equivalent to a molar yield of grafting of 67%.

Example 2

Modification in the Mass of a Polyisoprene by Grafting of 2,4,6-trimethyl-3-(2-(2-oxoimidazolidin-1-yl)ethoxy)nitrile oxide

2.1—Grafting of the Modifying Agent onto Polyisoprene Natsyn 2200 (Goodyear)

The same modifying agent as the one previously obtained in example 1 is used. 2.85 g of 2,4,6-trimethyl-3-(2-(2-oxoimidazolidin-1-yl)ethoxy)nitrile oxide, having an NMR purity of 86 mol %, are incorporated into 30 g of polyisoprene Natsyn 2200 ([ML(1+4) 100° C.=79, units 3,4=0.5%, units trans 1,4=1.9%, unit cis 1,4=97.6%, Mw=1044.10$^3$ g/mol, Vp=3.6]) on a cylinder tool (external mill at 30° C.). The mixture is homogenized in 15 passes.

This mixing phase is followed by a heat treatment in a press at a pressure of 10 bar. The durations and the temperatures of this second stage were modulated.

$^1$H NMR analysis made it possible to determine the molar amount of grafting and the molar yield of grafting which are reported in the following table:

TABLE 6

| time | T° | NMR level (mol%) | yield |
|---|---|---|---|
| 5 min | 130 | 1.52 | 88% |
| 10 min | 130 | 1.55 | 90% |
| 5 min | 150 | 1.54 | 90% |
| 10 min | 150 | 1.58 | 92% |

Example 3

Modification of an SBR by Grafting of 3-methoxy-4-[2-(2-oxoimidazolidin-1-yl)ethoxy]benzonitrile oxide

1.1—Preparation of the Modifying Agent a) Preparation of 3-methoxy-4-[2-(2-oxoimidazolidin-1-yl)ethoxy]benzonitrile oxide

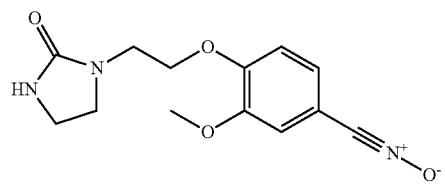 [SMILES: COc1cc(C#[N+][O-])ccc1OCCN1CCNC1=O]

This compound may be prepared from vanillin and 2-chloroethylimidazolidone according to the following synthesis scheme:

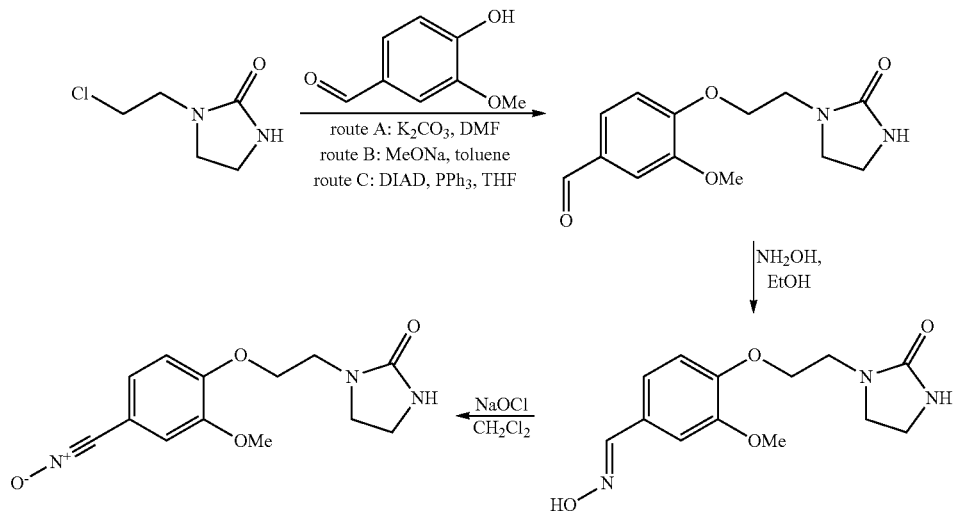

b) Preparation of 3-methoxy-4-[2-(2-oxoimidazolidin-1-yl)ethoxy]benzaldehyde

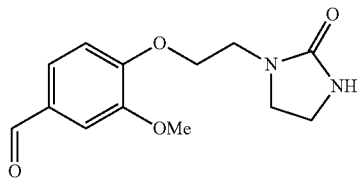 [SMILES: COc1cc(C=O)ccc1OCCN1CCNC1=O]

Route A

A suspension of vanillin (30.0 g, 0.197 mol) and of K$_2$CO$_3$ (95.4 g, 0.690 mol) in DMF (200 mL) is heated at 50° C. for 15 minutes. To this suspension is added in portions 1-(2-chloroethyl)imidazolidin-2-one (44.0 g, 0.296 mol, purity>90%), whose preparation has been described in example 1, in DMF (30 mL). The reaction medium is heated to 90° C. (T$_{bath}$) and this temperature is maintained for about 4 hours. The reaction medium is brought to room temperature and then water (1.25 L) is added. The product is extracted with CH$_2$Cl$_2$ (400 mL, 4 times 100 mL). The combined organic phases are washed with water (60 mL) and concentrated under reduced pressure (14 mbar, 40° C.). The crude reaction product is diluted with Et$_2$O (100 mL) and the suspension is stirred at room temperature for 15-20 minutes. The precipitate obtained is filtered, washed with Et$_2$O (3 times 15 mL) and dried at room temperature.

A solid (31.2 g, yield 60%) having a melting point of 130° C. is obtained.

The molar purity is greater than 92% ($^1$H NMR).
Route B

To a solution of sodium (1.51 g, 0.066 mol) in CH$_3$OH (60 mL) is added vanillin (10.0 g, 0.066 mol) in anhydrous toluene (250 mL). The reaction medium, under an inert atmosphere, is heated under reflux and then the residual methanol is distilled off. After returning to 80-90° C., a suspension of 1-(2-chloroethyl)imidazolidin-2-one (9.28 g, 0.064 mol, purity>95%) in toluene (50 mL) is added all at once to the reaction medium. After 25 hours of reaction, the reaction medium is concentrated under reduced pressure (T$_{bath}$ 50° C., 30 mbar). The crude reaction product is taken up in CH$_2$Cl$_2$ (150 mL). The unreacted vanillin is removed by extraction with a 7% aqueous NaOH solution (5 times 30 mL). The combined organic phases are washed with water (4 times 50 mL), dried under Na$_2$SO$_4$ and evaporated under reduced pressure (T$_{bath}$ 27° C., 20 mbar). The crude reaction product (4.81 g) is diluted with a mixture of petroleum ether and EtOAc and the precipitate obtained is filtered.

A solid (0.91 g, yield 6%) having a melting point of 127° C. is obtained.

The molar purity is greater than 81% ($^1$H NMR).
Route C

The procedure for the Mitsunobu reaction is for example described in the following references: Mitsunobu, O.; Yamada, Y. Bull. Chem. Soc. Japan 1967, 40, 2380-2382, The Use of Diethyl Azodicarboxylate and Triphenylphosphine in Synthesis and Transformation of Natural Products Mitsunobu, O. Synthesis 1981, 1-28, patent EP1149092 B1, 2003.

To a solution of vanillin (5.02 g, 0.033 mol), of anhydrous 1-(2-hydroxyethyl)imidazolidin-2-one (6.38 g, 0.049 mol, Aldrich) and of PPh$_3$ (13.1 g, 0.050 mol) in anhydrous THF (300 mL) at 2° C. is added dropwise, over 20 minutes, a diisopropyl azodicarboxylate solution (10.1 g, 0.050 mol, Aldrich) in anhydrous THF (150 mL). The reaction medium is stirred for 14 hours at room temperature and is then diluted with water (150 mL). The reaction medium is concentrated under reduced pressure (45 mbar, T$_{bath}$ 28° C.). The aqueous phase is extracted with EtOAc (3 times 200 mL). The combined organic phases are washed with a saturated aqueous NaCl solution and are then concentrated under reduced pressure in order to obtain a solution of 150 mL. The crude reaction product in solution is purified by column chromatography (SiO$_2$, eluent 1: EtOAc, eluent 2: EtOAc/EtOH=4/1, Rf of the product 0.36, Rf of Ph$_3$PO 0.71 in EtOAc: EtOH=5:1).

A solid (6.59 g, yield 76%) having a melting point of 130° C. is obtained.

The molar purity is greater than 88% ($^1$H NMR).

The 3-methoxy-4-[2-(2-oxoimidazolidin-1-yl)ethoxy]benzaldehyde obtained is used directly in the next stage without further purification.

$^1$H and $^{13}$C NMR Characterization

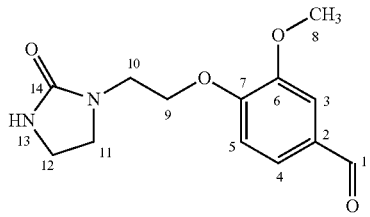 [SMILES: COc1cc(C=O)ccc1OCCN1CCNC1=O]

TABLE 7

| Atom No. | δ for $^1$H (ppm) | δ for $^{13}$C (ppm) |
|---|---|---|
| 1 | 9.78 | 191.1 |
| 2 | / | 129.6 |
| 3 | 7.34 | 109.6 |
| 4 | 7.48 | 125.6 |
| 5 | 7.14 | 112.0 |
| 6 | / | 148.9 |
| 7 | / | 152.9 |
| 8 | 3.78 | 55.4 |
| 9 | 4.11 | 67.3 |
| 10 | 3.42 | 45.5 |
| 11 | 3.38 | 42.3 |
| 12 | 3.16 | 37.2 |
| 13 | 6.33 | / |
| 14 | / | 161.9 |

Solvent used: DMSO - Calibration on the DMSO signal at 2.44 ppm for $^1$H, 39.5 ppm for $^{13}$C.

c) Preparation of 3-methoxy-4-[2-(2-oxoimidazolidin-1-yl)ethoxy]benzaldehyde oxime

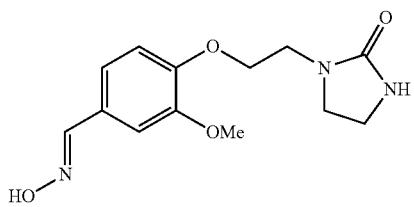 [SMILES: COc1cc(/C=N/O)ccc1OCCN1CCNC1=O]

To a solution of 3-methoxy-4-[2-(2-oxoimidazolidin-1-yl)ethoxy]benzaldehyde (25.6 g, 0.097 mol) in EtOH (250 mL) at 52° C. is added a solution of hydroxylamine (10.2 g, 0.155 mol, 50% in water, Aldrich) in EtOH (20 mL). The reaction medium is then stirred for 4.5 hours between 50 and 60° C. The reaction medium is then concentrated under reduced pressure (T$_{bath}$=42° C., 60 mbar) so as to obtain a residue of 70-80 mL. The precipitate obtained is filtered, washed with an EtOH/water mixture (twice 5 mL/15 mL) and dried under atmospheric pressure at room temperature.

A white solid (22.14 g, yield 82%) having a melting point of 189° C. is obtained.

The molar purity is greater than 89% ($^1$H NMR).

$^1$H and $^{13}$C NMR Characterization

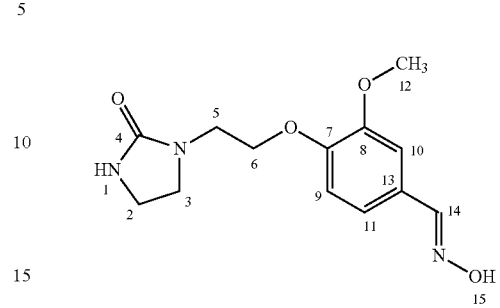

TABLE 8

| Atom No. | δ for $^1$H (ppm) | δ for $^{13}$C (ppm) |
|---|---|---|
| 1 | 6.30 | / |
| 2 | 3.16 | 37.1 |
| 3 | 3.35 | 42.4 |
| 4 | / | 161.9 |
| 5 | 3.42 | 45.4 |
| 6 | 4.00 | 67.0 |
| 7 | / | 148.5 |
| 8 | / | 148.9 |
| 9 | 6.93 | 112.8 |
| 10 | 7.15 | 108.6 |
| 11 | 7.01 | 119.9 |
| 12 | 3.72 | 55.2 |
| 13 | / | 125.9 |
| 14 | 7.98 | 147.5 |
| 15 | 10.92 | / |

Solvent used: DMSO - Calibration on the DMSO signal at 2.44 ppm for $^1$H, 39.5 ppm for $^{13}$C.

d) Preparation of 3-methoxy-4-[2-(2-oxoimidazolidin-1-yl)ethoxy]benzonitrile oxide

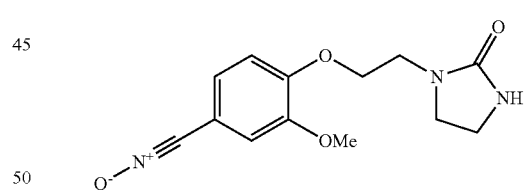

To a suspension of 3-methoxy-4-[2-(2-oxoimidazolidin-1-yl)ethoxy]benzaldehyde oxime (21.7 g, 0.078 mol) in CH$_2$Cl$_2$ (950 mL) at −3° C., is added dropwise an aqueous NaOCl solution in water (Aldrich, >4% of active chlorine) (161 mL) over 10 minutes. The reaction medium is then stirred for 20 minutes at 0° C. The organic phase is separated and the aqueous phase is extracted with CH$_2$Cl$_2$ (4 times 100 mL). The combined organic phases are washed with water (3 times 100 mL), dried over Na$_2$SO$_4$ and then concentrated under reduced pressure (T$_{bath}$ 22° C.) to 200-220 mL. The precipitate obtained is filtered, washed with CH$_2$Cl$_2$ (twice 10 mL) and dried under atmospheric pressure at room temperature.

A solid (9.13 g, yield 42%) having a melting point of 109-111° C. with degradation is obtained.

The molar purity is greater than 80% ($^1$H NMR). By recrystallization from EtOH, the purity of the compound is greater than 90 mass %.

$^1$H and $^{13}$C NMR Characterization

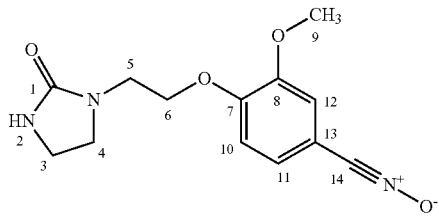 [SMILES: COc1cc(C#[N+][O-])ccc1OCCN1CCNC1=O]

TABLE 9

| Atom No. | δ for $^1$H (ppm) | δ for $^{13}$C (ppm) |
| --- | --- | --- |
| 1 | / | 163.5 |
| 2 | 6.31 | / |
| 3 | 3.15 | 37.2 |
| 4 | 3.35 | 42.3 |
| 5 | 3.40 | 45.4 |
| 6 | 4.04 | 67.1 |
| 7 | / | 150.4 |
| 8 | / | 148.4 |
| 9 | 3.73 | 55.6 |
| 10 | 7.03 | 113.0 |
| 11 | 7.25 | 125.8 |
| 12 | 7.32 | 115.2 |
| 13 | / | 106.2 |
| 14 | / | Not visible |

Solvent used: DMSO - Calibration on the DMSO signal at 2.44 ppm for $^1$H, 39.5 ppm for $^{13}$C.

Infrared Characterization (KBr Pellet)
ν (cm$^{-1}$): 2305 (function Ar—C≡N→O)
Characterization by Mass Spectrometry
$C_{13}H_{15}N_3O_4$, Mw=277.27 g/mol
The samples were analyzed by direct introduction in the mass spectrometer, using the electrospray ionization mode (DI/ESI).

Preparation of the Sample:
About 20 mg of sample were dissolved in 25 ml of methanol and then diluted to 1/100 for the DI/ESI analysis.

Positive Mode:
m/z: 300 ([[M+Na]$^+$), 577 ([2M+Na]$^+$)

1.2—Grafting of the Modifying Agent onto SBR in the Mass

The modifying agent previously obtained is used.
3-Methoxy-4-[2-(2-oxoimidazolidin-1-yl)ethoxy] benzonitrile oxide (1.24 g, 4.5 mmol), having an NMR purity of 90 mol % of SBR (containing 26% by weight of styrene and 24% by weight of a butadiene-1,2 unit and having an Mn=162 900 g/mol and a Vp=1.15) on a cylinder tool (external mill at 30° C.). The mixture is homogenized in 15 passes.

This mixing phase is followed by a heat treatment (10 min at 110° C.) in a press at a pressure of 10 bar.

The $^1$H NMR analysis made it possible to determine the molar amount of grafting (0.78 mol %) and the molar yield of grafting (87%).

Example 4

Modification of an SBR by Grafting of 2-[2-(2-oxoimidazolidin-1-yl)ethoxy]benzonitrile oxide 1.1—Preparation of the Modifying Agent a) Preparation of 2-[2-(2-oxoimidazolidin-1-yl)ethoxy]benzonitrile oxide

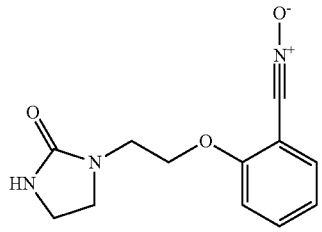 [SMILES: O=C1NCCN1CCOc1ccccc1C#[N+][O-]]

This compound may be prepared from salicylic aldehyde and 2-chloroethylimidazolidone according to the following synthesis scheme:

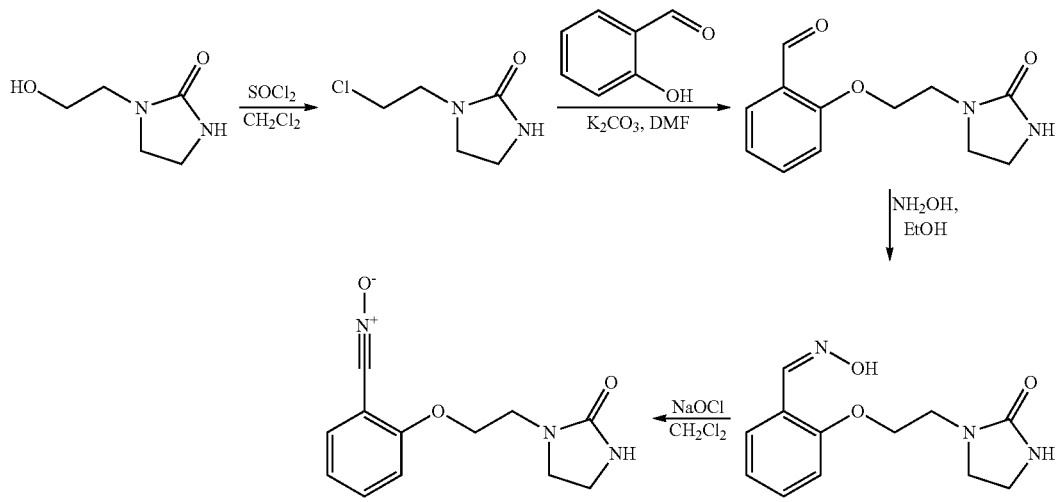

b) Preparation of 2-[2-(2-oxoimidazolidin-1-yl)ethoxy]benzaldehyde

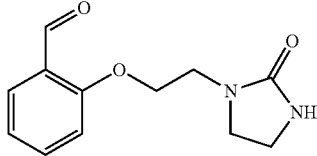 [SMILES: O=Cc1ccccc1OCCN1CCNC1=O]

To a solution of salicylic aldehyde (22.0 g, 0.180 mol) in DMF (100 mL) is added K$_2$CO$_3$ (87.1 g, 0.631 mol). The mixture is stirred at 52° C. After 10 minutes at this temperature, 1-(2-chloroethyl)imidazolidin-2-one (40.0 g, 0.270 mol, purity>90%) whose preparation has been described in example 1, is added in portions. The temperature of the mixture is brought to 90° C. (T$_{bath}$) over one hour and this temperature is maintained for 5 hours. After returning to room temperature, the mixture is diluted with water (1.3 L) and the product is extracted with CH$_2$Cl$_2$ (500 mL, 5 times 100 mL). The organic phases are combined, and then washed with water (twice 50 mL) and evaporated until a crude reaction product of 70-80 g is obtained (dense suspension) (T$_{bath}$=40° C.). The crude reaction product is taken up in Et$_2$O (120 mL) and the suspension is stirred at room temperature for 20 minutes. The precipitate obtained is filtered and washed with a DMF/Et$_2$O/H$_2$O mixture (5 mL/20 mL/15 mL) and then with Et$_2$O (twice 10 mL). The solid obtained is dried at room temperature.

A solid (30.6 g, yield 73%) having a melting point of 150° C. is obtained. The molar purity is greater than 84% ($^1$H NMR).

The 2-[2-(2-oxoimidazolidin-1-yl)ethoxy]benzaldehyde obtained is used directly in the next step without further purification.

$^1$H and $^{13}$C NMR Characterization

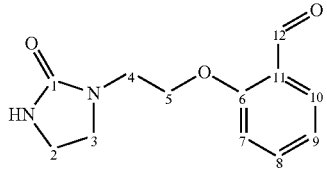

TABLE 10

| Atom | δ $^1$H (ppm) | δ $^{13}$C (ppm) |
|---|---|---|
| 1 | — | 164.9 |
| 2 | 3.15 | 37.3 |
| 3 | 3.39 | 44.9 |
| 4 | 3.44 | 42.1 |
| 5 | 4.16 | 66.5 |
| 6 | — | 160.5 |
| 7 | 7.17 | 113.2 |
| 8 | 7.59 | 136.2 |
| 9 | 7.02 | 120.5 |
| 10 | 7.63 | 127.3 |
| 11 | — | 124.0 |
| 12 | 10.31 | 189.1 |

Solvent used: DMSO - Calibration on the DMSO signal at 2.44 ppm for $^1$H, 39.5 ppm for $^{13}$C.

c) Preparation of 2-[2-(2-oxoimidazolidin-1-yl)ethoxy]benzaldehyde oxime

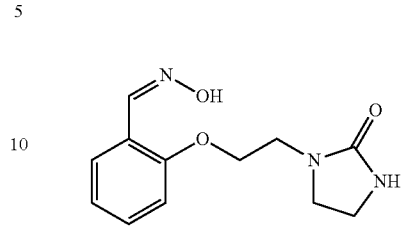

A solution of 2-[2-(2-oxoimidazolidin-1-yl)ethoxy]benzaldehyde (10.0 g, 0.043 mol) in EtOH (100 mL) is heated to 50° C. At this temperature, a hydroxylamine solution (4.5 g, 0.068 mol, 50% in water, Aldrich) in EtOH (10 mL) is added. The reaction medium is then stirred for 6 hours at a temperature between 50° C. and 70° C. The reaction medium is evaporated under reduced pressure (T$_{bath}$ 45° C., 65-70 mbar) until a suspension is obtained. The crude reaction product is then taken up in water (5 mL). The solution obtained is cooled to 5° C. and maintained at this temperature for 15 hours. The precipitate obtained is filtered and washed on the filter with an EtOH/water mixture (2 mL/2 mL) and then with an EtOH/petroleum ether mixture (1 mL/4 mL) and then with petroleum ether (2*10 mL). The solid is then dried under atmospheric pressure at room temperature.

A white solid (9.25 g, yield 87%) having a melting point of 88° C. is obtained.

The molar purity is greater than 99% ($^1$H NMR).

$^1$H and $^{13}$C NMR Characterization

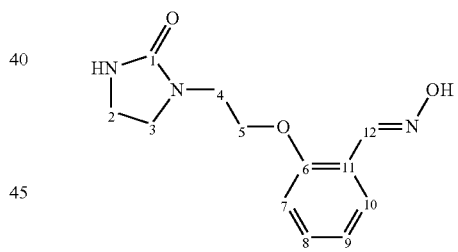

TABLE 11

| Atom | δ $^1$H (ppm) | δ $^{13}$C (ppm) |
|---|---|---|
| 1 | — | 162.0 |
| 2 | 3.17 | 37.4 |
| 3 | 3.37 | 45.4 |
| 4 | 3.39 | 42.6 |
| 5 | 4.03 | 66.6 |
| 8 | — | 155.8 |
| 7 | 7.01 | 113.0 |
| 8 | 7.28 | 130.7 |
| 9 | 6.89 | 121.2 |
| 10 | 7.61 | 125.2 |
| 11 | — | 120.9 |
| 12 | 8.25 | 143.3 |

Solvent used: DMSO - Calibration on the DMSO signal at 2.44 ppm for $^1$H, 39.5 ppm for $^{13}$C.

d) Preparation of 2-[2-(2-oxoimidazolidin-1-yl)ethoxy]benzonitrile oxide

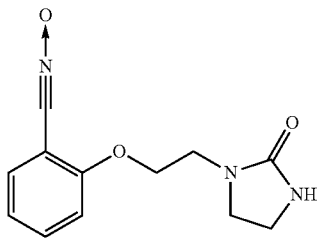 [SMILES: O=C1NCCN1CCOc1ccccc1C#[N+][O-]]

To a suspension of 2-[2-(2-oxoimidazolidin-1-yl)ethoxy] benzaldehyde oxime (20.2 g, 0.081 mol) in $CH_2Cl_2$ (400 mL) at −1° C. is added, dropwise over 10 minutes, an aqueous NaOCl solution in water (157 mL, Aldrich, >4% of active chlorine). The reaction medium is then stirred for 20 minutes. The aqueous and organic phases are separated and the aqueous phase is extracted with $CH_2Cl_2$ (twice 75 mL). The combined organic phases are washed with water (3 times 10 mL) and dried over $Na_2SO_4$. The phases are concentrated to 100 mL under reduced pressure at room temperature. 50 mL of petroleum ether are added. The solution is cooled to −18° C. (3 hours). The precipitate is filtered, washed with $CH_2Cl_2$/petroleum ether (5 mL/10 mL; then 5 mL/20 mL; then 0 mL/20 mL) and then dried under atmospheric pressure at room temperature.

A solid (11.32 g, yield 57%) having a melting point of 109-110° C. with degradation of the product is obtained.

The molar purity is greater than 94% ($^1$H NMR).

$^1$H and $^{13}$C NMR Characterization

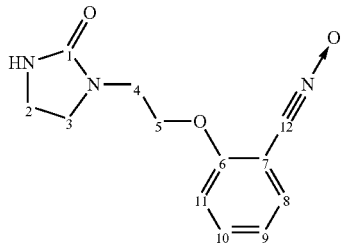

TABLE 12

| Atom | δ $^1$H (ppm) | δ $^{13}$C (ppm) |
|---|---|---|
| 1 | — | 162.0 |
| 2 | 3.18 | 37.5 |
| 3 | 3.45 | 45.8 |
| 4 | 3.39 | 42.5 |
| 5 | 4.14 | 67.9 |
| 6 | — | 159.9 |
| 7 | — | 101.6 |
| 8 | 7.60 | 133.4 |
| 9 | 7.00 | 121.2 |
| 10 | 7.48 | 132.9 |
| 11 | 7.16 | 112.6 |
| 12 | — | Not observed |
| NH | ~6.34 | — |

Solvent used: DMSO - Calibration on the DMSO signal at 2.44 ppm for $^1$H, 39.5 ppm for $^{13}$C.

Infrared Characterization (KBr Pellet)
ν ($cm^{-1}$): 2295 (function Ar—C≡N→O)
Characterization by Mass Spectrometry
$C_{12}H_{13}N_3O_3$, Mw=247.25 g/mol
The samples were analyzed by direct introduction into the mass spectrometer, using the electrospray ionization mode (DI/ESI).
Preparation of the Sample
20 mg of the sample are dissolved in 2 mL of acetonitrile
m/z: 270 ([[M+Na]$^+$), 517 ([2M+Na]$^+$)

1.2—Grafting of the Modifying Agent onto SBR in the Mass

The modifying agent previously obtained is used.

2-[2-(2-Oxoimidazolidin-1-yl)ethoxy]benzonitrile oxide (0.55 g, 2.24 mmol), having an NMR purity of 95 mol %, is incorporated into 30 g of SBR (containing 26% by weight of styrene and 24% by weight of butadiene-1,2 unit and having an Mn=162 900 g/mol and a Vp=1.15) on a cylinder tool (external mill at 30° C.). The mixture is homogenized in 15 passes.

This mixing phase is followed by a heat treatment (10 min at 110° C.) in a press at a pressure of 10 bar.

$^1$H NMR analysis made it possible to determine the molar amount of grafting (0.34 mol %) and the molar yield of grafting (71%).

The invention claimed is:
1. A modified polymer obtained by grafting of a compound comprising at least one group Q and at least one group A, bonded together by at least, one "spacer" group Sp in which:
   Q comprises a comprises a nitrile oxide, nitrone or nitrile imine functional group,
   A comprises an associative group comprising at least one nitrogen atom, and corresponds to one of the following formulae (II), (III), (IV), (V), or (VI):

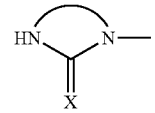

(II)

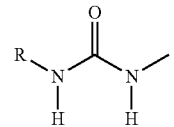

(III)

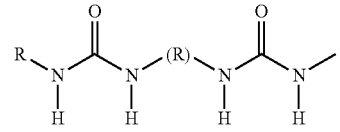

(IV)

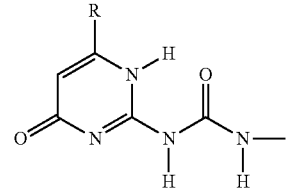

(V)

-continued (VI)
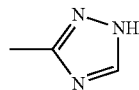

where:
R denotes a hydrocarbon group which may optionally contain heteroatoms,
X denotes an oxygen or sulphur atom or a group —NH
Sp is an atom or a group of atoms forming a bond between Q and A.

2. The modified polymer according to claim 1, wherein the polymer is a diene elastomer.

3. The modified polymer according to claim 2, wherein the diene elastomer is essentially saturated.

4. The modified polymer according to claim 2, wherein the diene elastomer is essentially unsaturated.

5. The modified polymer according to claim 1, wherein the group Q is a group of the following formula (VII), (VIII) or (IX)

(VII)
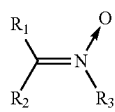

$R_4$—C≡N→O  (VIII)

$R_5$—C≡N→N—$R_6$  (IX)

in which R1 to R6 are independently selected from the group consisting of a spacer group Sp, a hydrogen atom, a linear or branched C1-C20 alkyl group, a linear or branched C3-C20 cycloalkyl group, a linear or branched C6-C20 aryl group and a group of formula (X)

(X)
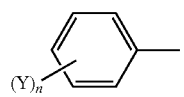

in which n represents 1, 2, 3, 4 or 5 and each Y independently represents a spacer group Sp, an alkyl group or a halide.

6. The modified polymer according to claim 1, wherein the "spacer" group is a linear or branched C1-C24 alkyl chain comprising one or more heteroatoms selected from nitrogen, sulphur, silicon or oxygen atoms.

7. The modified polymer according to claim 1, wherein the group Q is a group of formula (XIa) or (XIb):

(XIa)
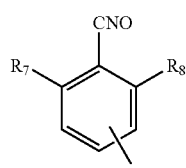

(XIb)
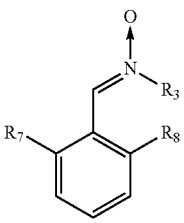

in which R7 and R8 independently represent a C1-C5 alkyl group or a halide and R3 is selected from the group consisting of a spacer group Sp, a hydrogen atom, a linear or branched C1-C20 alkyl group, a linear or branched C3-C20 cycloalkyl group, a linear or branched C6-C20 aryl group and a group of formula (X)

(X)
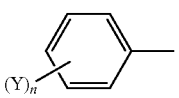

in which n represents 1, 2, 3, 4 or 5 and each Y independently represents a spacer group Sp, an alkyl group or a halide and the group A is a group of formula (XII)

(XII)
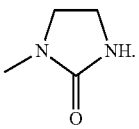

8. The modified polymer according to claim 1, wherein the compound is selected from the group consisting of compounds of the following formulae (XIII), (XIV), (XV), (XVI), (XVII), (XVIII), (XIX), (XX) and (XXI):

(XIII)
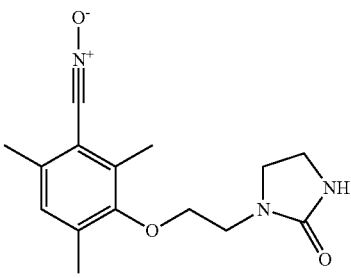

(XIV)
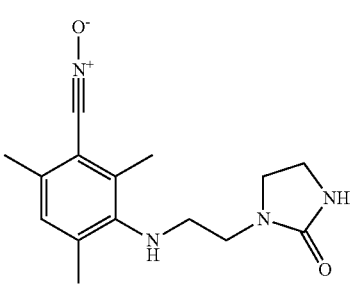

(XV)
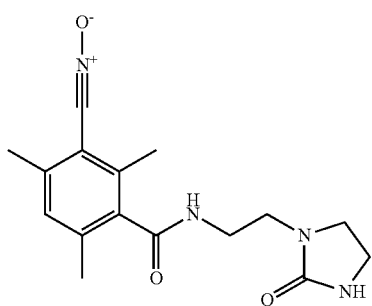

(XVI)
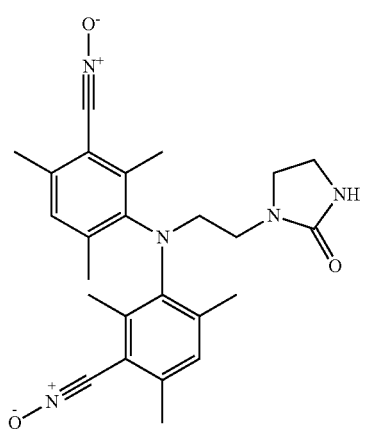

(XVII)
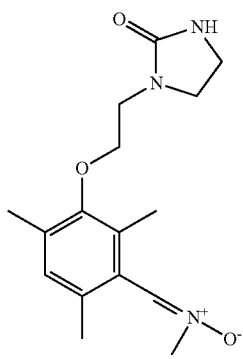

(XVIII)
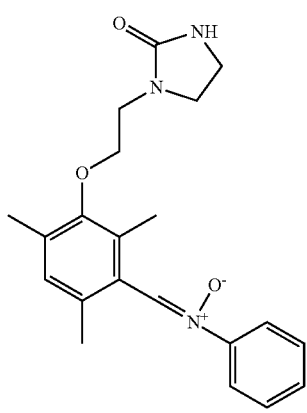

(XIX)
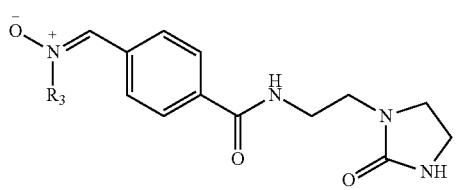

(XX)
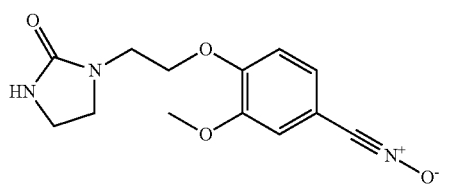

(XXI)
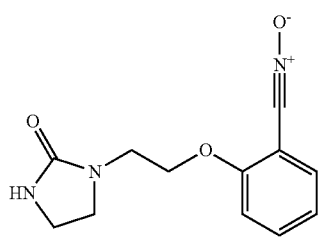

wherein R3 is selected from the group consisting of a spacer group Sp, a hydrogen atom, a linear or branched C1-C20 alkyl group, a linear or branched C3-C20 cycloalkyl group, a linear or branched C6-C20 aryl group and a group of formula (X)

(X)
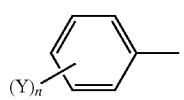

in which n represents 1, 2, 3, 4 or 5 and each Y independently represents a spacer group Sp, an alkyl group or a halide.

9. The modified polymer according to claim 1, wherein the compound is selected from the group consisting of compounds of the following formulae (XXII) and (XXIII)

(XXII)
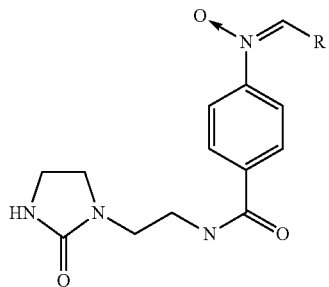

-continued

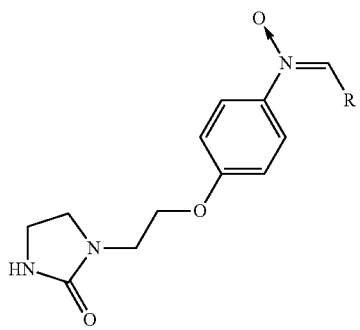
(XXIII)

in which R is independently selected from the group consisting of a spacer group Sp, a hydrogen atom, a linear or branched C1-C20 alkyl group, a linear or branched C3-C20 cycloalkyl group, a linear or branched C6-C20 aryl group, and a group of formula (X)

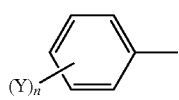
(X)

in which n represents 1, 2, 3, 4 or 5 and each Y independently represents a spacer group Sp, an alkyl group or a halide.

10. A process for the preparation of a modified polymer according to claim 1, comprising:
grafting onto a polymer comprising at least one unsaturation a compound comprising at least one group Q, and at least one group A bonded to each other by at least one "spacer" group Sp, wherein Q, A, and Sp are as defined in claim 1, by [3+2] cycloaddition of the group Q onto the unsaturation of the polymer.

11. The process for the preparation of a modified polymer according to claim 10, wherein the polymer is a diene elastomer.

12. The modified polymer according to claim 1, wherein there is one "spacer" group Sp.

13. The modified polymer according to claim 1, wherein X denotes an oxygen atom.

14. The modified polymer according to claim 3, wherein the diene elastomer is selected from the group consisting of ethylene-propylene-diene monomer (EPDM) copolymers and butyl rubbers.

15. The modified polymer according to claim 4, wherein the diene elastomer is selected from the group consisting of natural rubber, synthetic polyisoprenes, polybutadienes, butadiene copolymers, isoprene copolymers and mixtures of these elastomers.

16. The modified polymer according to claim 6, wherein the "spacer" group is a linear or branched C1-C10 alkyl chain comprising one or more heteroatoms selected from nitrogen, sulphur, silicon or oxygen atoms.

17. The modified polymer according to claim 7, wherein R7 and R8 each independently represent a methyl group or a chlorine atom.

* * * * *